(12) United States Patent
Phillips (10) Patent No.: US 9,572,704 B2
(45) Date of Patent: Feb. 21, 2017

(54) ANKLE FOOT ORTHOSIS

(71) Applicant: BONUTTI RESEARCH, INC., Effingham, IL (US)

(72) Inventor: Glen A. Phillips, Effingham, IL (US)

(73) Assignee: Bonutti Research, Inc., Effingham, IL (US)

( * ) Notice: Subject to any disclaimer, the term of this patent is extended or adjusted under 35 U.S.C. 154(b) by 0 days.

(21) Appl. No.: 15/149,875

(22) Filed: May 9, 2016

(65) Prior Publication Data

US 2016/0250060 A1 Sep. 1, 2016

Related U.S. Application Data

(63) Continuation of application No. 14/643,775, filed on Mar. 10, 2015, now Pat. No. 9,345,608, which is a continuation of application No. 13/873,467, filed on Apr. 29, 2013, now Pat. No. 8,998,834, which is a continuation of application No. 13/026,895, filed on Feb. 14, 2011, now Pat. No. 8,444,583.

(51) Int. Cl.
*A61F 5/00* (2006.01)
*A61F 5/01* (2006.01)

(52) U.S. Cl.
CPC ........... *A61F 5/0127* (2013.01); *A61F 5/0102* (2013.01); *A61F 2005/0139* (2013.01); *A61F 2005/0158* (2013.01)

(58) Field of Classification Search
CPC ...... A61F 2/3859; A61F 2/389; A61F 5/0102; A61F 2005/0139; A61F 2/38; A61F 2002/3895; A61F 2002/2817; A61F 2002/2835; A61F 2002/30079; A61F 2002/30326;A61F 2002/30364; A61F 2002/30382; A61F 5/013; A61F 2005/0155; A61F 2005/0153; A61F 2002/701; A61F 2002/7635; A61F 2/60; A61F 2/6607; A61F 2002/5003; A61F 2002/5007; A61F 2002/5018; A61F 2005/0179; A61F 5/0123; A61F 5/0125; A61F 2005/0172; A61F 5/0111; A61F 5/0118; A61F 2005/0165; A61F 5/055; A61F 2005/0137; A61F 5/012; A61F 2005/01
USPC .................. 602/16, 20–28; 128/882; 482/45
See application file for complete search history.

(56) References Cited

U.S. PATENT DOCUMENTS

4,955,370 A 9/1990 Pettine
5,399,147 A 3/1995 Kaiser
(Continued)

*Primary Examiner* — Michael Brown
(74) *Attorney, Agent, or Firm* — Senniger Powers LLP (57) ABSTRACT

An ankle foot orthosis includes a leg member, a foot member, and a drive member. The drive assembly includes a link member which may be hingedly secured to the foot member at a hinge location adjacent to the posterior end of the foot member. The drive assembly may be operable to selectively impart pivotal movement between the foot member and the link member about a first pivot axis, and pivotal movement between the foot member and the leg member about a second pivot axis at the hinge location. The leg member and the foot member strut may be selectively movable in a medial-lateral direction relative to a base of the foot member and the drive assembly. The inferior-superior location of the second pivot axis may be selectively adjustable for substantially aligning the second pivot axis with an axis of rotation of an ankle joint of the wearer.

14 Claims, 7 Drawing Sheets

(56) References Cited

U.S. PATENT DOCUMENTS

| | | | |
|---|---|---|---|
| 5,848,979 A * | 12/1998 | Bonutti | A61F 5/013 |
| | | | 482/45 |
| 5,891,061 A * | 4/1999 | Kaiser | A61F 5/0125 |
| | | | 601/33 |
| 6,171,272 B1 * | 1/2001 | Akita | A61F 5/0127 |
| | | | 602/27 |
| 6,752,774 B2 | 6/2004 | Townsend et al. | |
| 8,007,456 B2 | 8/2011 | Stano | |
| 8,192,434 B2 | 6/2012 | Huebner et al. | |
| 8,251,935 B2 | 8/2012 | Bonutti et al. | |
| 8,444,583 B2 | 5/2013 | Phillips | |
| 9,345,608 B2 | 5/2016 | Phillips | |
| 2006/0100561 A1 * | 5/2006 | Gilmour | A61F 5/0125 |
| | | | 602/26 |
| 2007/0219475 A1 | 9/2007 | Bonutti et al. | |
| 2008/0188356 A1 | 8/2008 | Bonutti et al. | |
| 2009/0227925 A1 | 9/2009 | McBean et al. | |
| 2011/0030698 A1 | 2/2011 | Kaufman et al. | |
| 2012/0209163 A1 | 8/2012 | Phillips | |
| 2013/0345611 A1 | 12/2013 | Phillips | |

* cited by examiner

ANKLE FOOT ORTHOSIS

CROSS REFERENCE TO RELATED APPLICATIONS

This patent application is a continuation of U.S. patent application Ser. No. 14/643,775, filed Mar. 10, 2015, which is continuation application of U.S. patent application Ser. No. 13/872,467, filed Apr. 29, 2013, issued as U.S. Pat. No. 8,998,834 on Apr. 7, 2015, which is a continuation application of U.S. patent application Ser. No. 13/026,895, filed Feb. 14, 2011, issued as U.S. Pat. No. 8,444,583 on May 21, 2013. The contents of the above-identified applications are herein incorporated by reference in their entirety.

BACKGROUND

The field of the invention relates generally to an ankle foot orthosis.

In a joint, the range of motion depends upon the anatomy of that joint and on the particular genetics of each individual. Typically, joints move in two directions, flexion and extension. Flexion is to bend the joint and extension is to straighten the joint. However, in the orthopedic convention some joints only flex. For example, the ankle has dorsiflexion and plantarflexion.

When a joint is injured either by trauma or by surgery, scar tissue can form, often resulting in flexion or extension contractures. Such conditions can limit the range of motion of the joint, limiting flexion (in the case of an extension contracture) or extension (in the case of a flexion contracture) of the injured joint. It is often possible to treat this condition by use of a range-of-motion (ROM) orthosis.

ROM orthoses are devices commonly used during physical rehabilitative therapy to increase the range-of-motion over which the patient can flex or extend the joint. Commercially available ROM orthoses are typically attached on opposite members of the joint and apply a torque to rotate the joint in opposition to the contraction. The force is gradually increased to increase the working range or angle of joint motion.

SUMMARY OF THE DISCLOSURE

In one aspect, an ankle foot orthosis generally comprises a leg member, a foot member, and a drive member. The leg member is configured to be releasably fastened to a leg of the wearer. The foot member is configured to be releasably fastened to a foot of a wearer, and the foot member has anterior and posterior ends. The drive assembly includes a link member hingedly secured to the foot member at a hinge location adjacent to the posterior end of the foot member. The drive assembly is operable to selectively impart pivotal movement between the foot member and the link member about a first pivot axis, and pivotal movement between the foot member and the leg member about a second pivot axis at the hinge location.

In another aspect, a method of treating an ankle joint using an ankle foot orthosis generally comprises fastening a foot member of the ankle foot orthosis to a foot of a wearer, and fastening a leg member of the ankle foot orthosis to a leg of the wearer. A drive assembly of the ankle foot orthosis is configured to impart pivotal movement between a link member of the drive assembly and the foot member about a first pivot axis located adjacent to a posterior end of the foot member, and to impart pivotal movement between the foot member and the leg member about a second pivot axis, to thereby impart one of dorsiflexion and plantarflexion of the ankle joint about a rotational axis.

In yet another aspect, an ankle foot orthosis generally comprises a leg member, a foot member, and a drive assembly. The leg member is configured to be releasably fastened to a leg of a wearer. The foot member is configured to be releasably fastened to a foot of the wearer. The foot member is hingedly connected to the leg member for pivotal movement between the foot member and the leg member about a pivot axis. The drive assembly is operable to selectively impart pivotal movement between the foot member and the leg member about the pivot axis. The inferior-superior location of the pivot axis is selectively adjustable for substantially aligning the pivot axis with an axis of rotation of an ankle joint of the wearer.

In another aspect, an ankle foot orthosis generally comprises a leg member, a foot member, and a drive assembly. The leg member is configured to be releasably fastened to a leg of a wearer. The foot member is configured to be releasably fastened to a foot of the wearer. The foot member includes a base and a foot member strut extending superiorly from the base. The foot member strut is hingedly connected to the leg member for pivotal movement between the foot member and the leg member about a pivot axis. The drive assembly is operable to selectively impart pivotal movement between the foot member and the leg member about the pivot axis. The leg member and the foot member strut are selectively movable in a medial-lateral direction relative to the base of the foot member and the drive assembly.

DETAILED DESCRIPTION OF THE DRAWINGS

Figure 1:
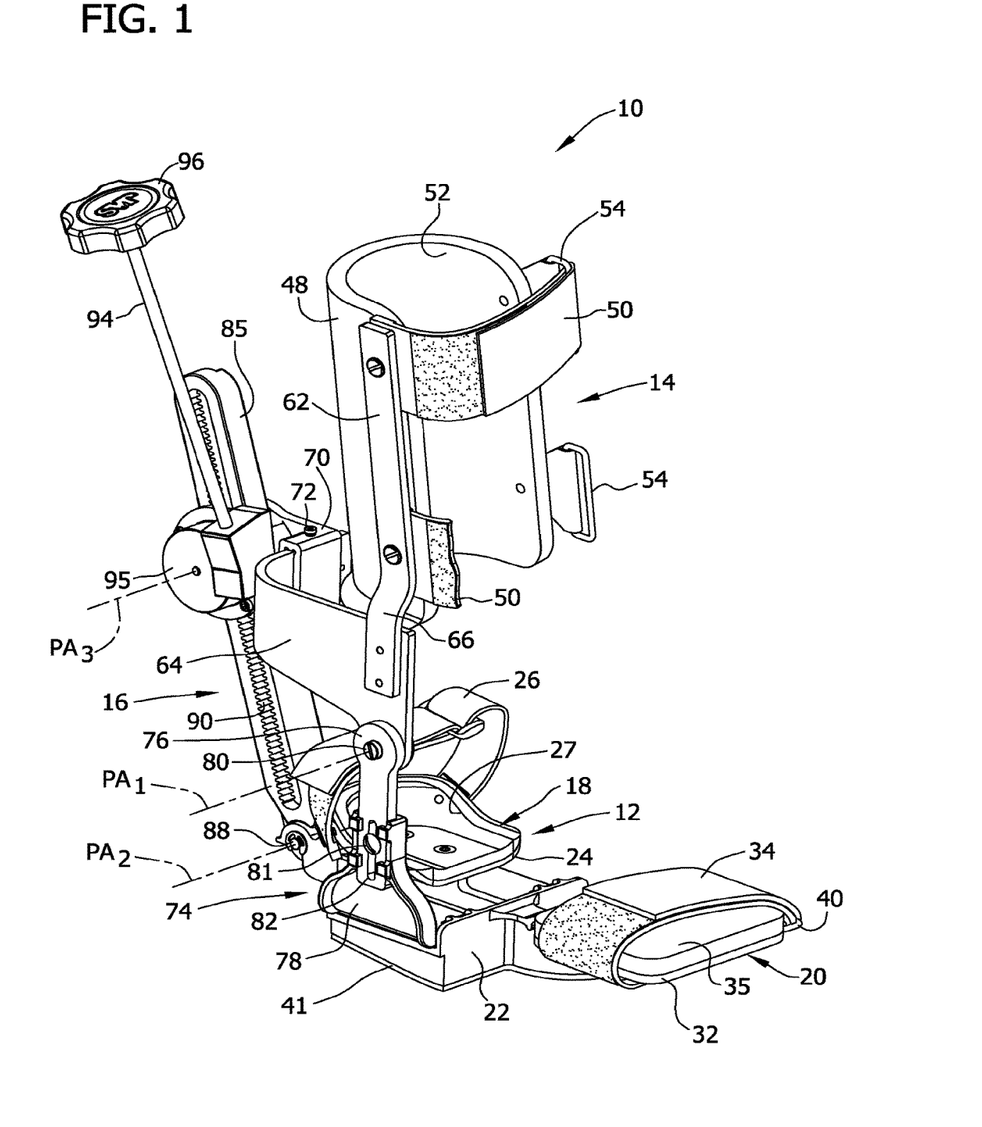
FIG. 1 is a perspective of one embodiment of an ankle foot orthosis.
Figure 2:
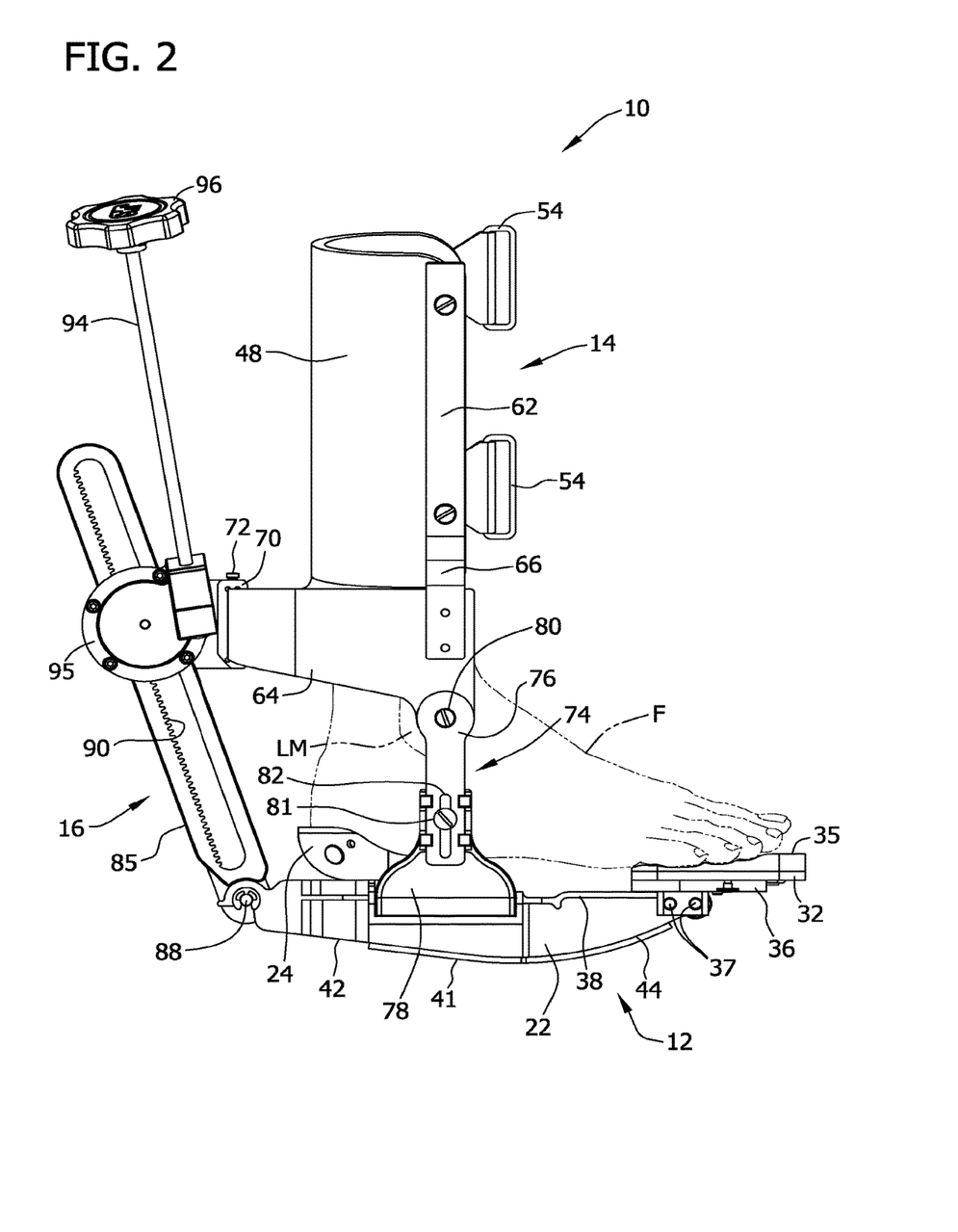
FIG. 2 is a left elevational view of the ankle foot orthosis fastened to a foot (in phantom), with straps being removed therefrom for illustrative purposes.
Figure 3:
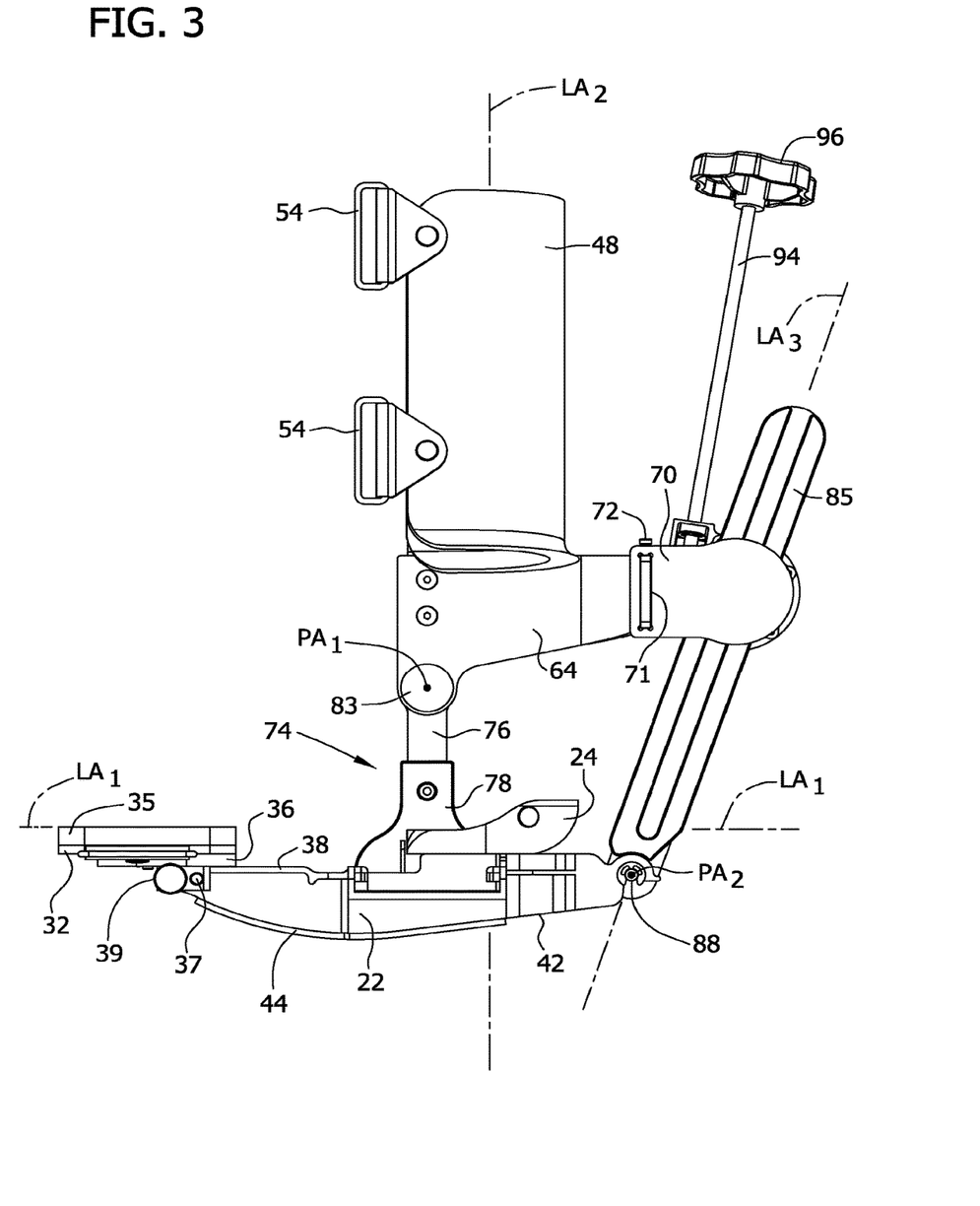
FIG. 3 is a right elevational view of the ankle foot orthosis, with straps being removed therefrom for illustrative purposes.

Referring now to the drawings, and in particular to FIGS. 1-3, an ankle foot orthosis for use in treating an ankle joint (i.e., a talocrural joint) of a wearer is generally indicated at 10. The illustrated ankle foot orthosis 10 includes a foot member, generally indicated at 12, which is releasably fastenable to a foot F of a wearer, a leg member, generally indicated at 14, which is releasably fastenable to a leg of a wearer, and a drive assembly, generally indicated at 16, for facilitating relative angular movement between the foot member and the leg member. As used in the following description, terms (e.g., inferior, superior, medial, lateral, anterior, and posterior, among others) relating to the locations, positions, and/or directions of components, structures, surfaces, and/or axes, among others, of the ankle foot orthosis 10 are human anatomical terms describing relative locations, positions, and/or directions when the ankle foot orthosis 10 is secured to the wearer.

As explained in more detail below, operation of the drive assembly 16 provides passive range-of-motion (ROM) treatment or exercise of the ankle joint of the wearer. In particular, the illustrated ankle foot orthosis 10 facilitates dorsiflexion and plantarflexion of the ankle joint and selective positioning of the ankle in dorsiflexion and plantarflexion. Dorsiflexion is movement of the dorsum (superior surface) of the foot F toward the leg about the ankle joint, thereby decreasing the angle between the dorsum of the foot F and the leg. Plantarflexion is movement of the dorsum of the foot F away from the leg, thereby increasing the angle between the dorsum of the foot F and the leg. As used herein, the ankle joint is in a neutral position when the angle between the plantar aspect of the foot F (lying generally within an anterior-posterior plane) and a longitudinal axis of the leg (lying generally within an inferior-superior plane) is about 90 degrees. The ankle joint is in a dorsiflexion position when the angle between the plantar aspect of the foot F and the longitudinal axis of the leg is less than about 90 degrees. The ankle joint is in a plantarflexion position when the angle between the plantar aspect of the foot F and the longitudinal axis of the leg is greater than about 90 degrees. The respective degrees of dorsiflexion and plantarflexion of the ankle joint are relative to the neutral position of the ankle joint. As seen in FIG. 2, the illustrated ankle foot orthosis 10 is shown fastened to a right lower limb of the wearer for treating a right ankle joint of the wearer, however, it is understood that the illustrated ankle foot orthosis may be fastened to a left lower limb of the wearer for treating a left ankle of the wearer.

Referring to FIGS. 1-4 and 6, the foot member 12 includes a heel securement assembly 18, and a forefoot securement assembly 20, both of which are connected to a generally rigid base 22. Together, the heel securement assembly 18 and the forefoot securement assembly 20 constitute a foot securement assembly. Although in the illustrated embodiment the heel and forefoot assemblies 18, 20, respectively, are formed as separate components, the two assemblies may be formed as a one-piece unit within the scope of the present disclosure. The foot member 12 has a longitudinal axis $LA_1$ (FIG. 3) extending in an anterior-posterior direction. The heel securement assembly 18 is disposed generally adjacent to a posterior end of the base 22, and the forefoot securement assembly 20 is disposed generally adjacent to an anterior end of the base. In the illustrated embodiment, the heel securement assembly 18 includes a heel cup 24, which at least partially receives and supports the heel of the wearer, and a strap 26 (FIGS. 1 and 6) secured to the heel cup. In the illustrated embodiment, the heel cup 24 is fixedly secured to the base 22, although the heel cup may be selectively movable (i.e., selectively slidable) on the base to adjust the position of the heel cup on the base. In the illustrated embodiment, the heel cup 24 has a generally low profile and is sized and shaped such that a posterior portion of the heel cup 24 does not contact the wearer's Achilles tendon. The heel cup 24 may include a pad 27 or may otherwise be provided with cushioning material for comfort.

Figure 6:
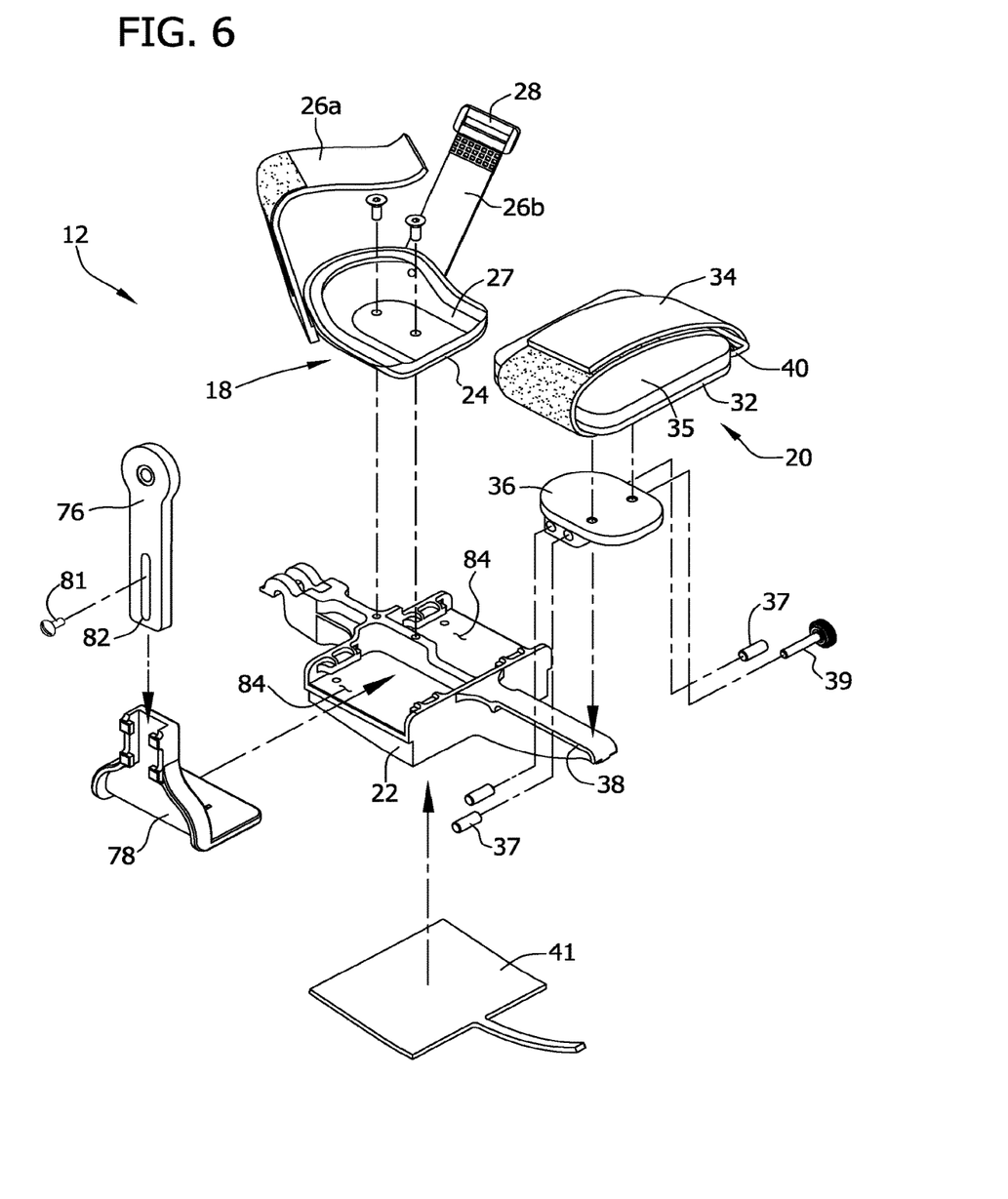
FIG. 6 is an enlarged, exploded view of the foot member of the ankle foot orthosis.

Referring to FIGS. 1 and 6, the strap 26 of the heel securement assembly 18 is extendable over the foot F of the wearer, generally adjacent to the wearer's ankle, when the wearer's heel is received in the heel cup 24 to releasably fasten the cup to the wearer's heel. As seen best in FIG. 6, the illustrated strap 26 is of a two-piece construction including a first strap component 26a that loops through a D-ring 28 of a second strap component 26b. The first strap component 26a includes fastening components, such as hook and loop components, so that the strap 26 is adjustable and may be tightened over the wearer's foot F. A pad or other cushioning component may be provided on the strap 26 to provide comfort. The heel securement assembly 18 may have other configurations, and other ways of releasably fastening the foot member 12 to the heel of the wearer are within the scope of the present disclosure.

Referring to FIGS. 1-4 and 6, the forefoot securement assembly 20 includes a forefoot plate 32 for supporting the forefoot of the wearer, and a strap 34 (FIGS. 1 and 6) secured to the forefoot plate. The forefoot plate 32 includes a pad 35, which has a generally planar support surface on which the forefoot of the wearer rests. The illustrated pad 35 provides cushioning and comfort to the person, although the forefoot plate 32 may not include a cushioning pad. In the illustrated embodiment, the forefoot plate 32 is selectively movable on the base 22 in an anterior-posterior direction to accommodate feet having different lengths. As seen best in FIGS. 2, 3 and 6, the forefoot plate 32 is secured to a carriage 36. The carriage 36 includes pins 37 that slidably retain the carriage on a flange or rail 38 of the base 22. A locking device (e.g., a thumb screw 39 in the illustrated embodiment) facilitates selective locking of the carriage 36, and thus the forefoot plate 32, in a selected anterior-posterior position on the base 22. Other ways of making the forefoot securement assembly 20 selectively movable do not depart from the scope of the present disclosure. Moreover, the forefoot securement assembly 20 may not be selectively movable without departing from the scope of the present disclosure.

The illustrated strap 34 of the forefoot securement assembly 20 is looped through a D-ring 40 attached to the forefoot plate 32. The strap 34 includes a releasable fastening component, such as hook and look components, to adjustably tighten the strap and releasably fasten the forefoot of the wearer to the plate 32. The forefoot securement assembly 20 may have other configurations, and other ways of releasably fastening the forefoot of the wearer to the foot member 12 are within the scope of the present disclosure.

Referring particularly to FIG. 6, the base 22 of the foot member 12 may be formed from a rigid plastic material or from another suitable material. In one embodiment, the base 22 is constructed to support weight of a wearer's lower limb when the wearer is seated and the base is contacting a floor or other foot support surface, as this is the preferred position of the wearer when treating the ankle joint using the ankle foot orthosis 10. It is understood, however, that the wearer may be in a lying position or another position while the ankle foot orthosis 10 applies treatment. An outsole member 41 is secured to a bottom (i.e., inferior surface) of the base 18. The outsole member 20 is made of a suitable material, such as non-skid polyethylene or other suitable material, to inhibit the foot member 12 from sliding on the floor or other foot support surface.

In the illustrated embodiment, the bottom surface of the base 22 has posterior and anterior portions, 42, 44, respective. The posterior portion 42 extends from adjacent the posterior end of the base 22 to a location intermediate the posterior and anterior ends of the base. The posterior portion 42 is generally planar and is intended to contact and rest on a planar floor or other support surface. In the illustrated embodiment, the posterior portion 42 lies in a plane that is angularly offset from (i.e., non-parallel to) the plane defined by the support surface of the forefoot securement assembly 20 (e.g., the superior surface of the pad 35). For example, the posterior portion 42 may lie in a plane that is angularly offset between about 10° and about 30°. In this way, when the foot F of the wearer is fastened to the ankle foot orthosis 10 and the contact portion 42 of the bottom surface of the base 22 is resting on a planar support surface, the foot F extends upward at an angle relative to the planar support surface that is substantially equal to the angular offset between the posterior portion 42 and the plane defined by the support surface of the forefoot securement assembly 20. The anterior portion 44 of the bottom surface of the base 22 extends from adjacent the posterior portion 42 to adjacent the anterior end of the base. The anterior portion 44 is generally convex or arcuate to enhance strength of the base 22. It is understood that the bottom surface of the base 22, and the base in general, may be of other configurations without departing from the scope of the present disclosure.

Referring to FIGS. 1-5, the leg member 14 includes a leg cuff 48 adapted to receive and partially encircle a circumference of a leg of the wearer, and a pair of straps 50 (FIG. 1) secured to the leg cuff for releasably fastening the leg cuff to the leg. The leg cuff 48 has a longitudinal axis $LA_2$ (FIG. 3) extending in an inferior-superior direction and extends along the length of the wearer's leg when the cuff is fastened to the leg. The leg cuff 48 may be formed from plastic or other material and include a pad 52, or other cushioning material, to provide comfort to the person. Each strap 50 is looped through a D-ring 54 secured to the leg cuff 48, and each strap includes releasable fastening components, such as hook and loop components, so that the straps are adjustable to tighten the straps over the wearer's leg. The leg member 14 may be of other configurations, and other ways of releasably fastening the leg member 14 to the leg of the wearer are within the scope of the present disclosure.

Referring still to FIGS. 1-5, the leg member 14 includes a strut 62 attached to a side of the leg cuff 48, and a bracket 64 connecting the leg member strut to the drive assembly 16. The leg member strut 62 is generally rigid and elongate, and may be made from metal or other material. The leg member strut 62 is fixedly secured to, such as by fasteners (e.g., screws), the side of the leg cuff 48, and is fixedly secured to the bracket 64, such as by screws 65 (FIG. 5) or other fasteners or in other ways. Although the leg member strut 62 is substantially rigid, the strut has a bendable portion 66 adjacent to the bracket 64. The bendable portion 66 is pre-bent and bendable in a generally medial-lateral direction to accommodate wearers having different degrees of varus/valgus of the knee. Although the illustrated ankle foot orthosis 10 includes a single leg member strut 62, in another embodiment the ankle foot orthosis may include one or more additional leg member struts secured to the other side of the leg member 14 or at other locations on the leg member without departing from the scope of the present disclosure.

Figure 4:
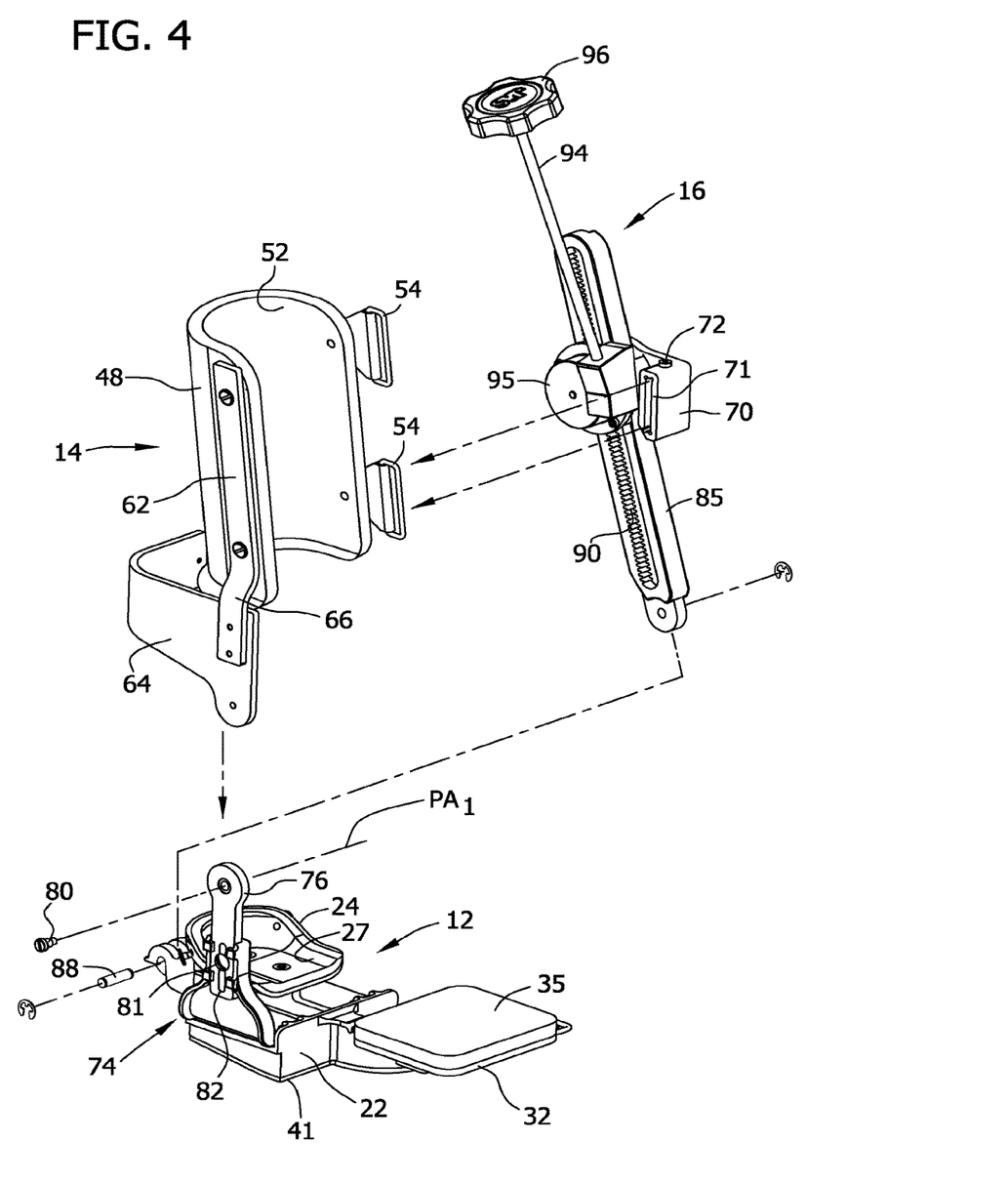
FIG. 4 is an exploded view of the ankle foot orthosis, a foot member, a leg member and a drive assembly being exploded from one another.
Figure 5:
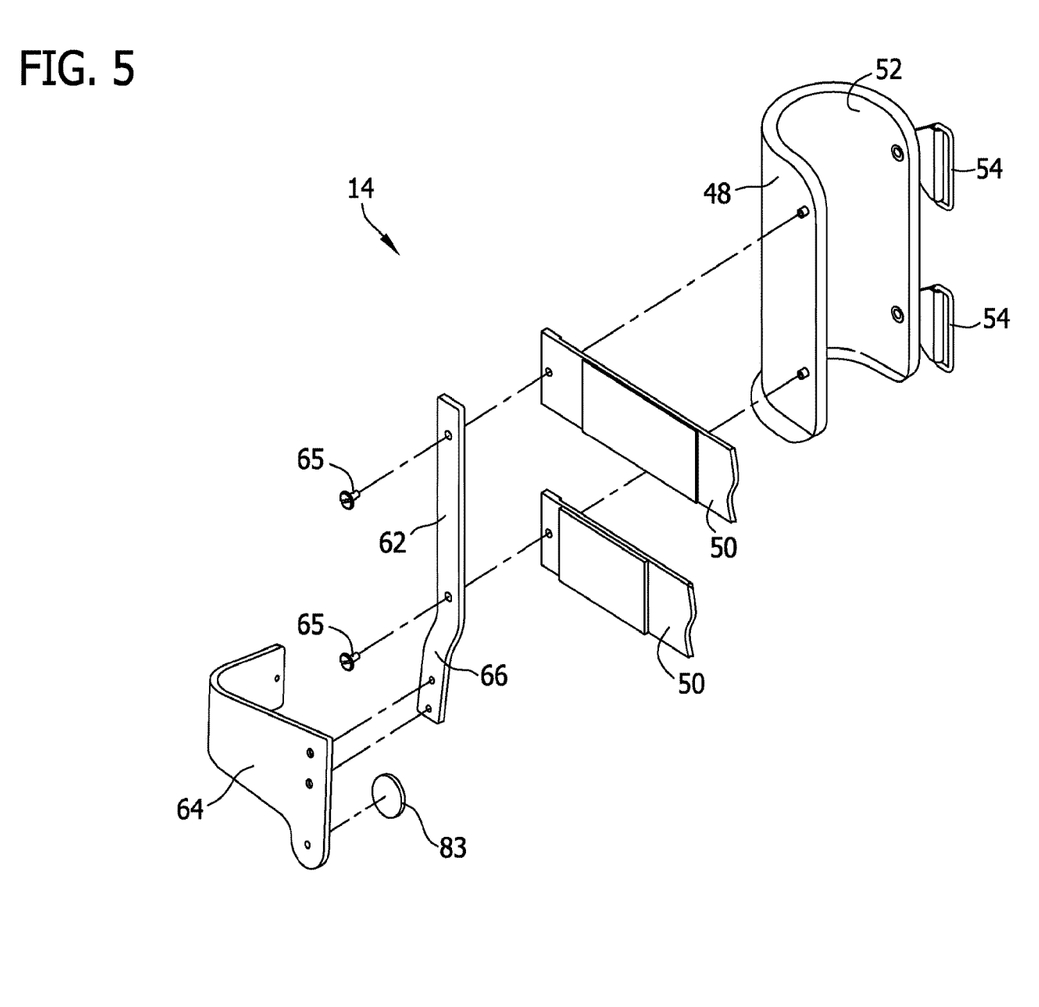
FIG. 5 is an enlarged, exploded view of the leg member of the ankle foot orthosis.

As seen best in FIGS. 1 and 5, the illustrated bracket 64 is generally L-shaped having a lateral portion (broadly, a first portion) extending posteriorly from the leg member strut 62, and a posterior portion (broadly, a second portion) extending medially from a posterior end of the lateral portion. As seen best in FIGS. 1-3, the leg member strut 62 is fixedly attached to the lateral portion of the bracket 64, and the posterior portion of the bracket is slidably attached to a bracket securement component 70 of the drive assembly 16. More specifically, the posterior portion of the bracket 64 is slidably received in a slot-shaped opening 71 (FIG. 4) of the bracket securement component 70, whereby the bracket 64 is capable of selectively sliding laterally relative to the drive assembly 16. A locking device, which is in the form of a set screw 72 in the illustrated embodiment, facilitates selective locking and unlocking of the bracket 64 in a selected medial-lateral position relative to the drive assembly 16. Through this configuration and for purposes explained in more detail below, the leg member 14 is capable of moving in a medial-lateral direction relative to the foot member 12 and the drive assembly 16. Other ways of allowing the leg member 14 to be selectively moved in the medial-lateral direction relative to the foot member 12 and the drive assembly 16 do not depart from the scope of the present disclosure. Moreover, it is understood that the leg member 14 may not be selectively movable in the medial-lateral direction relative to the foot member 12 and the drive assembly 16 without departing from the scope of the present disclosure Referring now to FIGS. 1-4 and 6, the illustrated foot member 12 includes a strut, generally indicated at 74, that is hingedly secured to the bracket 64, more specifically the lateral portion of the bracket, to allow for pivotal movement between the leg member 14 and the foot member 12 about a pivot axis $PA_1$ (FIGS. 3 and 4). As explained in more detail below, the pivot axis $PA_1$ lies in a generally medial-lateral plane and is preferably substantially coaxial with the rotational axis of the ankle joint during use. The foot member strut 74 is generally L-shaped and extends from the bracket 64 to the base 22 of the foot member 12, below (inferior to) the heel cup 24. The foot member strut 74 is constructed as a two-piece assembly, including a superior component 76 (broadly, a first component) and an inferior component 78 (broadly, a second component). The superior component 76 is hingedly secured, such as by a shoulder screw 80 or a pin, to the lateral portion of the bracket 64. It is understood that the foot member strut 74 may be hingedly secured to the leg member strut 62 in an embodiment which does not include the bracket 64. It is understood that the ankle foot orthosis 10 may not include the foot member strut and/or the leg member strut 62 without departing from the scope of the present disclosure. In such an example, the leg member 14 and the foot member 12 would still be pivotable, relative to one another, about the pivot axis $PA_1$, but the leg member and the foot member would not be hingedly connected to one another at the pivot axis.

In the illustrated embodiment, the superior component 76 is selectively slidable relative to the inferior component 78 in a generally inferior-superior direction to facilitate selective alignment of the pivot axis $PA_1$ with the rotational axis of the ankle joint. Aligning the pivot axis $PA_1$ with the rotational axis of the ankle joint reduces ankle compression and minimizes the occurrence of the heel lifting off the heel cup 24 during operation of the drive assembly 16. The superior component 76 is lockable in a selected inferior-superior position using a locking device 81, which in the illustrated embodiment is in the form of a screw received in a slot-shaped opening 82 of the superior component. A malleolus pad 83 is attached to the inner side of the superior component at the pivotal axis to provide comfort and prevent chaffing of skin at the ankle. In the illustrated embodiment, the malleolus pad 83 is positioned adjacent the lateral malleolus LM, although it is understood that in other embodiments the malleolus pad may be adjacent the medial malleolus. It is understood that the foot member strut 74 may be a one-piece component and/or non-adjustable in length in the inferior-superior direction without departing from the scope of the present disclosure.

The inferior component 78 is generally L-shaped and is slidably connected to the base 22 of the foot member 12. The inferior component 78 is received in a track 84 defined by the base and is freely slidable relative to the foot member 12 such that medial-lateral movement of the bracket 64 imparts sliding medial-lateral movement of the foot member strut 74 relative to the foot member. Thus, the leg cuff 48, the leg member strut 66, the bracket 64, and the foot member strut 74 are movable together in a medial-lateral direction. In this way, the ankle foot orthosis 10 can be adjusted based on the thickness (i.e., a medial-lateral dimension) of the lateral portion of the wearer's lower leg and ankle to facilitate proper positioning of the wearer's heel and forefoot on the foot member 12. For example, the wearer may have swelling (i.e., edema) of the ankle and/or an ankle wrap or bandage around his/her ankle. In such a situation, the bracket 64 may be slid relative to the bracket securement component 70 to allow the wearer to properly position his/her heel and forefoot on the foot member 12.

In the illustrated embodiment, the base 22 has two tracks 84 on opposite sides of the base, although only one of the tracks is used, depending on whether the orthosis is configured for the right ankle or the left ankle. In this way, the base is modular, wherein only one type of base needs to be manufactured for both a right ankle foot orthosis and a left ankle foot orthosis. In a left ankle foot orthosis, the foot member strut 74 is received in the other track. The inferior component 78 may be made from plastic or other material. In another embodiment, a locking device (not shown) may be associated with the inferior component 78 to prevent unintended sliding of the inferior component relative to the foot member 12.

Referring to FIGS. 1-4 and 7, the drive assembly 16 is generally in the form of a rack and pinion drive assembly. Accordingly, the drive assembly 16 includes a rack 85, and a pinion 86 operably coupled to the rack. The ankle foot orthosis 10 may include other types of drive assemblies besides the illustrated rack and pinion drive assembly 16. The rack 85, which broadly constitutes a link member, is hingedly secured to the foot member 12 at a securement location generally adjacent to the posterior end of the base 22. The rack 85 is hingedly connected to the foot member 12 by a pin 88 so that the rack is pivotable about a pivot axis $PA_2$ (FIGS. 1 and 3). The rack 85 may be hingedly secured to the foot member 12 in other ways. The rack 85 is generally elongate, having a longitudinal axis $LA_3$ (FIG. 3) extending slightly posteriorly from adjacent the posterior end of the base 22 of the foot member 12 and superiorly toward the leg cuff 48. The longitudinal axis $LA_3$ of the rack 85 is disposed posterior to the heel cup 24 and the leg member 14, and is generally coplanar with the longitudinal axis $LA_1$ of the foot member 12, such that when the wearer's heel is fastened to the heel cup 24, the Achilles tendon of the wearer is also generally coplanar with the longitudinal axis $LA_3$ of the rack 85.

The rack 85 includes a plurality of teeth 90 extending substantially linearly along the length of the rack. The pinion 86 operably engages the teeth 90 of the rack 85, whereby rotation of the pinion imparts relative movement between the pinion and the rack, which, in turn, imparts pivotal movement between the rack and the foot member 12 about the pivot axis $PA_2$ and imparts pivotal movement between the foot member and the leg member 14 about the pivot axis $PA_1$, as explained in more detail below. In the illustrated embodiment, the teeth 90 define a linear longitudinal axis that is generally coplanar with the longitudinal axis $LA_1$ of the foot member 12, and when the wearer's heel is fastened to the heel cup 24, the teeth are generally coplanar with the Achilles tendon of the wearer. Through the configuration and position of the drive assembly 16, the drive assembly provides a force directly to the foot member 12 to create a moment about the pivot axis $PA_1$ and the rotational axis of the ankle joint.

Figure 7:
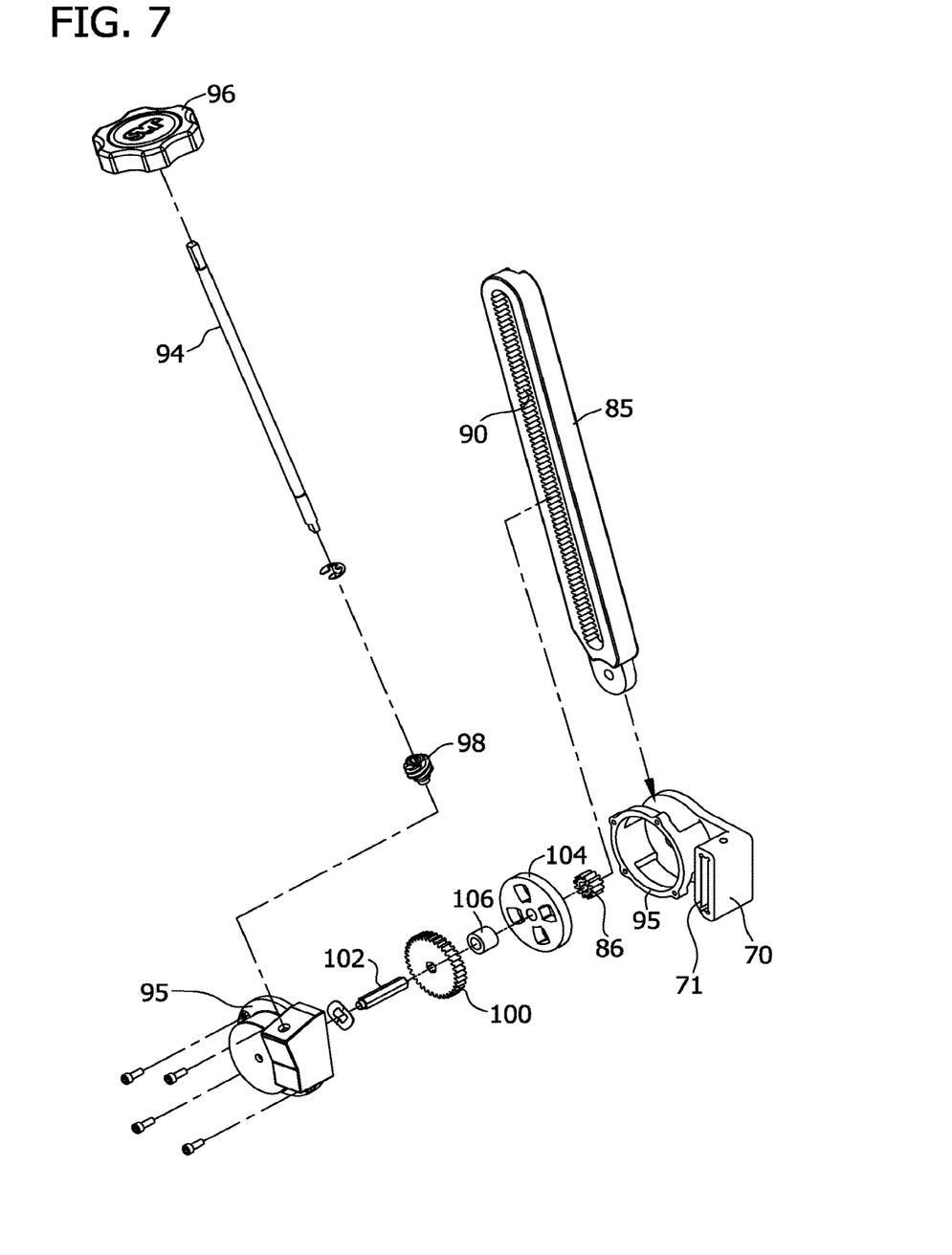
FIG. 7 is an enlarged, exploded view of the drive assembly of the ankle foot orthosis.

As seen best in FIG. 7, rotation of the pinion 86 is driven by a manually rotatable input shaft 94 secured to a gear box 95 that is slidably secured to the rack 85 and moves with the rack. In the illustrated embodiment, the bracket securement component 70 is attached to the gear box 95 and moves with the gear box. The gear box 95 and the rack 85 are pivotable relative to one another about a pivot axis $PA_3$. As such, rotation of the pinion 86 also imparts relative pivotal movement between the gear box 95 (and the securement component 70) and the rack 85. The input shaft 94 has a knob 96 secured at a superior longitudinal end and a worm 98 secured at an inferior longitudinal end, which is received in the gear box 95. The input shaft 94 extends superiorly from the gear box 95 at a lateral angle relative to the longitudinal axis $LA_3$ of the rack 85. Through this configuration, the knob 96 is adjacent the lateral side of the leg cuff 48, as positioned on the right lower limb in the illustrated embodiment, so that the knob 96 is accessible to the wearer using his/her right hand, in the illustrated embodiment, when the wearer is seated. It is understood that the knob 96 may be adjacent the medial side of the leg cuff 48, as positioned on a right lower limb or a left lower limb, without departing from the scope of the present invention. Within the gear box 95, the worm 98 operably engages a worm gear 100, which is coaxially secured to the pinion 86 via a drive shaft 102 (e.g., a hexagonal shaft). The worm gear 100 has a diameter larger than the diameter of the pinion 86 to provide a mechanical advantage. A bushing 104 for the drive shaft 102 is disposed between the worm gear 100 and the pinion 86. The drive shaft 102 passes through the bushing 104 and a spacer 106 that spaces the bushing apart from the worm gear 100. The bushing engages the inner surface of the gear box 95 to inhibit canting or slanting of the drive shaft, thereby retaining the worm gear 100 and the pinion 86 in operative engagement with the worm 98 and the rack 85, respectively. The drive assembly 16 may have other configurations without departing from the scope of the present disclosure.

In one exemplary method of using the ankle foot orthosis 10, the wearer's foot F and leg are placed in the orthosis. The wearer's foot F is placed in the orthosis 10 by placing the heel in the heel cup 24 and placing the forefoot on the forefoot plate 32. The forefoot plate 32 may be slidably adjusted, such as by loosening the set screw 36 and sliding the forefoot plate on the base 22, so that the strap 34 extends over the toes and the toes do not extend past the anterior edge of the plate. The wearer's leg is inserted into the leg cuff 48, such as by spreading apart the lateral and medial sides to allow the leg to enter the cuff. The medial-lateral position of the leg cuff 48, the bracket 64, and the foot member strut 74 relative to the wearer's foot F (and the foot member 12 and the drive assembly 16) may be adjusted to accommodate the thickness of the inferior portion of the wearer's leg and ankle. The set screw 72 is loosened to allow the bracket 64 to slide freely relative to the bracket securement component 70. When the leg cuff 48, the bracket 64, and the foot member strut 74 are in the selected medial-lateral position, the set screw 72 is tightened.

The inferior-superior position of the pivot axis $PA_1$ can be adjusted if the pivot axis is not substantially coaxial with the rotational axis of the ankle joint. The inferior-superior position of the pivot axis $PA_1$ is adjusted by loosening the screw 81 connecting the superior component 76 to the inferior component 78 of the foot strut 66, and then sliding the superior component either superiorly or inferiorly relative to the inferior component. The screw 81 is tightened when the pivot axis $PA_1$ is coaxial with the rotational axis of the ankle joint. Alignment of the pivot axis $PA_1$ with the rotational axis of the ankle joint may be accomplished by substantially aligning the pin 80, and the malleolus pad 83 with the lateral malleolus LM, in the illustrated embodiment, or the medial malleolus in another embodiment.

After the confirming that the wearer's leg and foot F are properly positioned in the ankle foot orthosis 10, the straps 26, 34 of the foot member 12 and the straps 50 of the leg member 48 are tightened to fasten the ankle foot orthosis to the foot F and leg of the wearer. With the ankle foot orthosis 10 fastened to the wearer's leg and foot F and the wearer preferably seated, the knob 96 is rotated, either by the wearer or another person, to provide passive range-of-motion (ROM) exercise of the ankle joint. In particular, rotation of the knob 96 in a selected direction decreases the spacing between the pinion 86 and the pivot axis $PA_2$, causing respective pivoting movement between the rack 85 and the foot member 12 about the pivot axis $PA_2$, and between the bracket 64 (and the leg cuff 48) and the foot member 12 about pivot axis $PA_1$, to thereby impart plantarflexion of the ankle joint. Rotation of the knob 96 in a selected, opposite direction increases the spacing between the pinion 86 and the pivot axis $PA_2$, causing respective pivoting movement between the rack 85 and the foot member 12 about the pivot axis $PA_2$, and between the bracket 64 (and the leg cuff 48) and the foot member 12 about the pivot axis $PA_1$, to thereby impart dorsiflexion of the ankle joint. In one embodiment, the drive assembly 16 of the ankle foot orthosis 10 is configured to facilitate movement and positioning of the ankle joint from about 0 degrees to about 40 degrees of dorsiflexion and from about 0 degrees to about 52 degrees of plantarflexion.

In one treatment protocol, the ankle joint may be moved to a first position in one of dorsiflexion and plantarflexion for a predetermined amount of time (e.g., about 5 minutes), and then the drive assembly 16 is operated to move the ankle joint to a second position in said one of dorsiflexion and plantarflexion of another predetermined amount of time (e.g., another 5 minutes). The drive assembly 16 may also be operated to move the ankle joint any number of subsequent positions. Maintaining the ankle joint in the first and second positions and any other subsequent positions for the predetermined amount of time allows connective tissue of the ankle joint to be stretched. In particular, this type of treatment utilizes the principles of stress relaxation to stretch the connective tissue of the joint. In another embodiment, the ankle foot orthosis 10 may also be configured to provide a dynamic stretch to the ankle joint.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An orthosis for increasing range of motion of a joint, the orthosis comprising:
    a first body securement portion configured to secure to a first body portion on a first side of the joint, wherein the first body securement portion comprises a cuff having an open front side for receiving the first body portion, a closed back side, and opposite left and right sides;
    a second body securement portion configured to secure to a second body portion on a second side of the joint;
    a drive assembly operatively connected to the first and second body securement portions, wherein the drive assembly is configured to drive movement of the first and second body securement portions relative to one another; and
    an L-shaped bracket operatively connecting the first body securement portion to the drive assembly, wherein the L-shaped bracket is selectively movable relative to the drive assembly to adjust a position of the first body portion relative to the drive assembly, wherein the L-shaped bracket includes a first arm at one of the left and right sides of the cuff and extending rearwardly, and a second arm extending generally perpendicularly from a rear end of the first arm and disposed rearward of the closed back side of the cuff.

2. The orthosis set forth in claim 1, wherein the cuff includes a pad and a strap configured to extend over the open front side to secure the first body portion in the cuff.

3. The orthosis set forth in claim 2, wherein the cuff is a leg cuff.

4. The orthosis set forth in claim 1, wherein the first arm is operatively connected to the first body securement portion and the second arm is operatively connected to the drive assembly.

5. The orthosis set forth in claim 4, wherein the second arm extends in a first direction, wherein the L-shaped bracket is selectively movable relative to the drive assembly in the first direction.

6. The orthosis set forth in claim 5, further comprising a locking device configured to selectively lock the L-shaped bracket in a selected position relative to the drive assembly, and unlock the L-shaped bracket to allow movement of the L-shaped bracket relative to the drive assembly.

7. The orthosis set forth in claim 6, wherein the locking device comprises a screw.

8. The orthosis set forth in claim 1, further comprising a second L-shaped bracket operatively connecting the second body securement portion to the drive assembly.

9. The orthosis set forth in claim 1, wherein the L-shaped bracket is selectively movable relative to the second body securement portion.

10. The orthosis set forth in claim 1, wherein the first and second body securement portions are operatively coupled to one another at a hinge connection.

11. The orthosis set forth in claim 1, further comprising a locking device configured to selectively lock the L-shaped bracket in a selected position relative to the drive assembly, and unlock the L-shaped bracket to allow movement of the L-shaped bracket relative to the drive assembly.

12. The orthosis set forth in claim 11, wherein the L-shaped bracket is selectively movable relative to the second body securement portion.

13. The orthosis set forth in claim 1, wherein the drive assembly comprises a worm and a worm gear engaging the worm.

14. The orthosis set forth in claim 13, wherein the drive assembly comprises an input shaft having a first longitudinal end connected to the worm, and a knob connected to a second longitudinal end of the input shaft.

* * * * *

UNITED STATES PATENT AND TRADEMARK OFFICE
CERTIFICATE OF CORRECTION

| | | |
|---|---|---|
| PATENT NO. | : 9,572,704 B2 | Page 1 of 1 |
| APPLICATION NO. | : 15/149875 | |
| DATED | : February 21, 2017 | |
| INVENTOR(S) | : Glen A. Phillips | |

It is certified that error appears in the above-identified patent and that said Letters Patent is hereby corrected as shown below:

On the Title Page

Item (63), Related U.S. Application Data reads:
"continuation of application No. 13/873,467"

Should read:
--continuation of application No. 13/872,467--

Signed and Sealed this
Second Day of May, 2017

Michelle K. Lee
*Director of the United States Patent and Trademark Office*